United States Patent
Wise

(10) Patent No.: US 11,991,416 B2
(45) Date of Patent: *May 21, 2024

(54) AUTHENTICATED STREAM MANIPULATION

(71) Applicant: Tailstream Technologies, LLC, Chicago, IL (US)

(72) Inventor: Kelley Wise, Villa Park, CA (US)

(73) Assignee: TailStream Technologies, LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/504,162

(22) Filed: Oct. 18, 2021

(65) Prior Publication Data

US 2022/0038785 A1  Feb. 3, 2022

Related U.S. Application Data

(63) Continuation of application No. 16/737,592, filed on Jan. 8, 2020, now Pat. No. 11,153,656, which is a continuation of application No. 12/058,977, filed on Mar. 31, 2008, now abandoned.

(60) Provisional application No. 60/911,811, filed on Apr. 13, 2007.

(51) Int. Cl.
| | |
|---|---|
| *H04N 21/472* | (2011.01) |
| *H04L 65/61* | (2022.01) |
| *H04L 65/612* | (2022.01) |
| *H04L 65/75* | (2022.01) |
| *H04N 21/462* | (2011.01) |
| *H04N 21/4627* | (2011.01) |
| *H04N 21/637* | (2011.01) |
| *H04N 21/6373* | (2011.01) |

(52) U.S. Cl.
CPC ..... *H04N 21/47205* (2013.01); *H04L 65/612* (2022.05); *H04L 65/75* (2022.05); *H04N 21/4627* (2013.01); *H04N 21/47202* (2013.01); *H04N 21/6373* (2013.01)

(58) Field of Classification Search
CPC ......... H04N 21/47205; H04N 21/4627; H04N 21/47202; H04N 21/6373; H04L 65/612; H04L 65/75
USPC ........................................................... 725/87
See application file for complete search history.

(56) References Cited

U.S. PATENT DOCUMENTS

| | | | |
|---|---|---|---|
| 7,191,217 B2 | 3/2007 | Tanabe | 709/205 |
| 7,213,266 B1 | 5/2007 | Maher | 726/26 |
| 7,234,064 B2 | 6/2007 | Menschik | 713/193 |
| 7,376,710 B1 * | 5/2008 | Cromwell | H04L 65/612 |
| | | | 709/219 |
| 7,664,708 B2 | 2/2010 | Stefik | 705/59 |

(Continued)

FOREIGN PATENT DOCUMENTS

| | | |
|---|---|---|
| EP | 1376980 B1 | 1/2004 |
| KR | 100467929 B1 | 3/2003 |
| KR | 100493900 B1 | 3/2005 |

*Primary Examiner* — Dominic D Saltarelli
(74) *Attorney, Agent, or Firm* — Niro McAndrews, LLP

(57) ABSTRACT

Systems and methods for accessing a media stream are presented. In response to a request for a media stream, an individual can be authorized to manipulate the media stream. Once an individual has gained authorization with respect to a media stream's manipulation rights, they are allowed to manipulate the stream. In some embodiments, a provider controls a secure environment to play the stream and enforce the rights.

18 Claims, 3 Drawing Sheets

(56) References Cited

U.S. PATENT DOCUMENTS

| | | | |
|---|---|---|---|
| 7,735,144 B2 | 6/2010 | Pravetz | 726/30 |
| 7,890,985 B2 | 2/2011 | Bowra | 725/88 |
| 7,904,707 B2 | 3/2011 | Shear | 713/2 |
| 8,230,098 B2 | 7/2012 | Chen | 709/231 |
| 8,255,331 B2 | 8/2012 | Risan | 705/50 |
| 8,266,659 B2 * | 9/2012 | Urdang | H04N 21/235 725/89 |
| 8,429,211 B1 * | 4/2013 | Shaffer | H04L 65/612 707/913 |
| 8,601,277 B2 | 12/2013 | Asami | 713/182 |
| 9,356,824 B1 * | 5/2016 | Khanal | H04L 61/45 |
| 2002/0194492 A1 | 12/2002 | Choi | 726/26 |
| 2003/0195932 A1 | 10/2003 | Tanabe | 709/205 |
| 2004/0003269 A1 | 1/2004 | Waxma | 713/193 |
| 2004/0230891 A1 | 11/2004 | Pravetz | 715/229 |
| 2005/0027995 A1 | 2/2005 | Menschik | 713/193 |
| 2005/0177716 A1 | 8/2005 | Ginter | 713/157 |
| 2005/0216417 A1 | 9/2005 | Risan | 705/52 |
| 2006/0037037 A1 | 2/2006 | Miranz | 725/2 |
| 2006/0080539 A1 | 4/2006 | Asami | 713/182 |
| 2006/0083485 A1 * | 4/2006 | Kikuchi | H04N 9/8227 386/E9.013 |
| 2006/0271484 A1 | 11/2006 | Stefik | 705/51 |
| 2007/0064943 A1 | 3/2007 | Ginter | 380/233 |
| 2007/0266169 A1 | 11/2007 | Chen | 709/231 |
| 2007/0271106 A1 | 11/2007 | Lee | 705/51 |
| 2007/0271388 A1 | 11/2007 | Bowra | 709/231 |
| 2007/0288764 A1 | 12/2007 | Shear | 713/190 |
| 2008/0037951 A1 * | 2/2008 | Cho | H04N 21/47202 386/278 |

* cited by examiner

AUTHENTICATED STREAM MANIPULATION

CROSS-REFERENCE TO CO-PENDING APPLICATION

This application is a continuation of U.S. patent application Ser. No. 16/737,592 titled Authenticated Stream Manipulation that was filed on Jan. 8, 2020, issued on Oct. 19, 2021 as U.S. Pat. No. 11,153,656, and was a continuation of U.S. patent application Ser. No. 12/058,977 titled Authenticated Stream Manipulation that was filed on Mar. 31, 2008 and claimed priority to U.S. Provisional Patent Application 60/911,811 that was filed on Apr. 13, 2007, the contents of which are all herein incorporated by reference.

FIELD OF THE INVENTION

The field of the invention is media stream manipulation technologies.

BACKGROUND OF THE INVENTION

In many markets access to media streams is heavily restricted by digital rights management (DRM) issues ensure only authorized individuals are allowed to access the digital data. For example, in medical markets, digital patient medical records are secured to ensure that only authorized medial professionals or institutions can access the records. Providing such systems for authentication aids in protecting a patient's privacy.

Most medial record distribution systems provide for accessing patient data where the data is stored at the source of the data. For example, U.S. Pat. No. 7,234,064 to Menschik et al. describes a peer-to-peer networked patient data distribution system having a centralized database of meta-data describing available patient data. Individuals authenticate against the centralized database to search for available patient records. The individual can then access a desired patient record directly from a remote source in peer-to-peer exchange rather than from the central database.

The '064 patent, as well as other similar distributions systems, continue to follow the trend of offering access to media stream without allowing an individual to manipulate the media stream. In markets such as the medical market, great care is taken to ensure medical records are not altered. However, it has not yet been appreciated that there are reasons to offer rights to manipulate a media stream in an environment where one would ordinarily desire to keep the media stream intact.

To continue with the medical market example, it would be advantageous to offer medical professionals the ability to manipulate media streams relating to patient data. For example, an oncologist could obtain authorization to add annotations to a media stream representing a MM scanning session while retaining the integrity of the media stream. The annotations could be added as an audio track to the media stream corresponding to the MRI scanning session.

Others have contemplated providing support for various aspects of digital rights management (DRM). For example, U.S. Pat. No. 7,213,266 to Maher el al. provides for systems and methods for managing electronic content and applications. Applications, content, and/or users can be given credentials that indicate compliance to a set of requirements pertaining to how the applications and content should interact. Once the credentials are validated, the applications and content can then be used. Although useful for ensuring that applications or content can interoperate effectively, Maher fails to contemplate providing a set of manipulation rights to allow manipulation of a media stream.

U.S. Pat. No. 7,191,217 to Tanabe et al. describes a proxy server that comprises a manipulation right controller that gives a manipulation right to execute an application within a distributed sever-based collaborative computing environment. However, Tanabe contemplates that manipulation rights provide for executing an application as opposed to manipulating a media stream by altering the flow or content of the stream.

Thus, there is still a need for systems and methods by which for an individual is able to obtain authorization to manipulate a media stream with respect to acquired manipulation rights.

SUMMARY OF THE INVENTION

The present invention provides apparatus, systems and methods in which an individual requests a media stream and receives authorization to exercise a set of one or more manipulation rights. The individual is allowed to manipulate the media stream to within the boundaries of manipulation rights.

In one aspect, an individual requests the media stream from a provider. The provider sends the media stream to the individual where the stream is played within a secure environment. Preferably the secure environment remains under control of the provider and ensures any manipulation rights associated with the media stream are enforced.

As used herein, the term "individual" is used euphemistically to reference an entity that can be authenticated. In a preferred embodiment, an individual represents an individual associated with healthcare. For example, healthcare individuals can include medical professionals, insurance professionals, medical practices, or others associated with the healthcare profession. However, it should be appreciated that that an individual could be a single person, a company, an affiliation, a group, a software module or application, or other entity capable of being identified or otherwise authenticated.

A media stream represents a flow a data that can be played. In a preferred embodiment, the media stream comprises content that can be played over a period of time. Example preferred media streams include videos, moving images, slide shows, audio data, live sessions, games, sensor data, or other sequentially played data. In a yet more preferred embodiment, the content includes medical data (e.g., visualization data, diagnostic data, insurance claim information, etc. . . . ).

Manipulation rights refer to rights that relate to altering of data. Manipulation rights of a data stream can include altering the flow of the stream, altering content of the stream, or other alteration.

Various objects, features, aspects and advantages of the inventive subject matter will become more apparent from the following detailed description of preferred embodiments, along with the accompanying drawings in which like numerals represent like components.

DETAILED DESCRIPTION

The following detailed description illustrates various embodiments of the inventive subject matter within the light of the medical industry. Such examples should be not considered limiting. It is also contemplated that the disclosed techniques can be applied with little or no modification to alternative markets beyond the medical industry. For example, one could use the described techniques within video or audio editing environments where remote editors are authorized to alter media streams.

Media Stream System Overview

Figure 1:
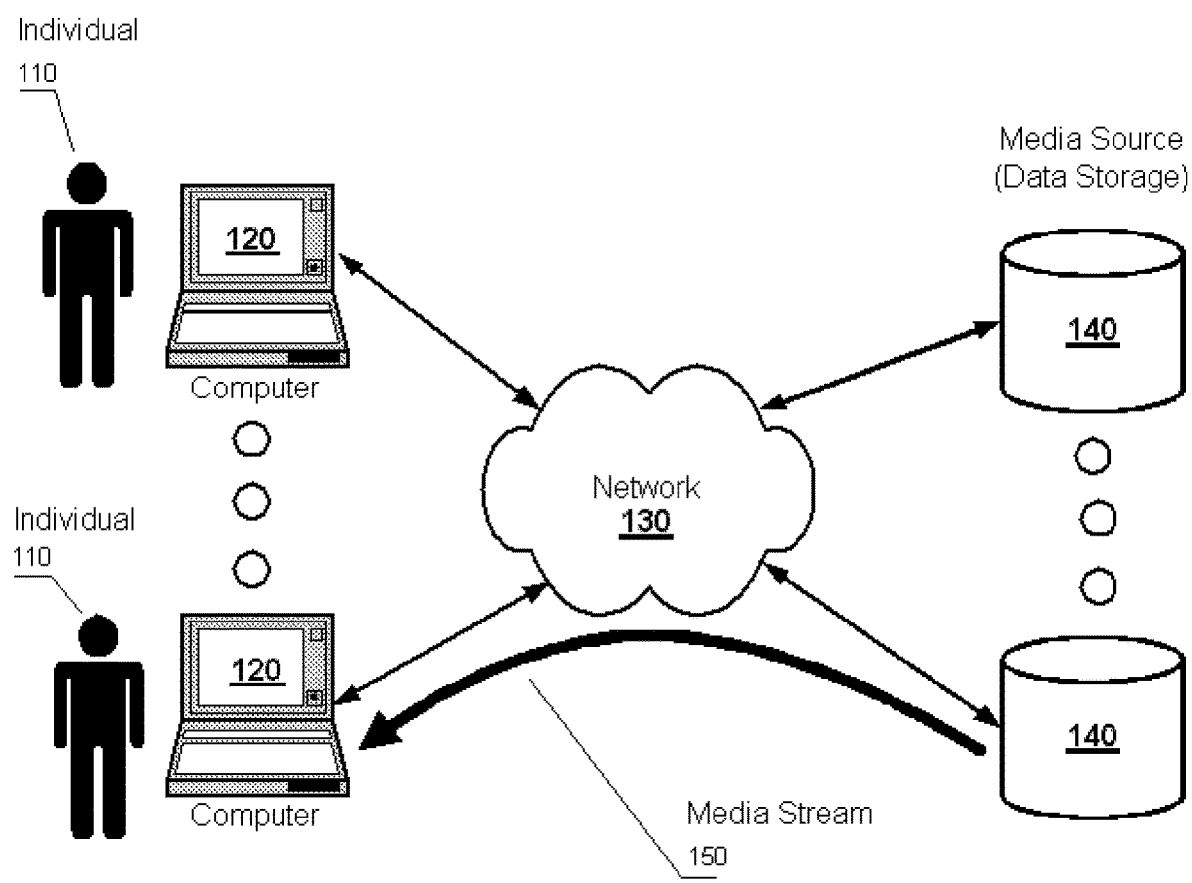
FIG. 1 is a schematic of an example system where an individual accesses a media stream.

In FIG. 1 an individual 110 uses computer 120 to access media stream 150 over network 130 from a provider storing media stream 150 on media source 140. In a preferred embodiment, individual 110 includes a medical professional or medical institution that has access rights to media stream 150. Individual 110 submits a request to a provider for media stream 150 where the request can include a search query, database search, or simply a call to application program interface (API).

Media stream 150 originates from media source 140 where, in some embodiments, media stream 150 can be stored as a digital data file within a data storage system. The data storage system can include a database, web server, network attached storage, storage area network, a computer readable memory, or other digital data storage system.

It is also contemplated, that media source 140 could include a live feed from one or more sensors. Preferred sensors include medial equipment adapted to capture or record data from a patient. In embodiments targeting other markets beyond the medical industry sensors can include a camera or even a microphone. Capturing live media feeds allows an individual to access data real-time. For medical applications, real-time capture of patient data can improve the odds of the patient's survival, especially in emergency situations.

Network 130 connects computer 120 to media source 140 and provides communication path between two systems. Network 130 can comprise known networks including a peer-to-peer network, the Internet, a WAN, a LAN, a VLAN, a VPN, a satellite network, a cell phone network, television, or other communication network. One should note that it is also contemplated that computer 120 could comprise media source 140 which would reduce a need for network 130.

Media stream 150 can include nearly any data that can be streamed. In a preferred embodiment, media stream 150 comprises medical data. In some embodiments, media stream 150 can be encrypted using well known cipher suites (e.g., PKI, AES, 3DES, SSL, HTTPS, SSH, etc. . . . ) or those yet to be invented to ensure confidentially of the steamed data.

Although media stream 150 is contemplated to comprise traditional media streams including video, audio, slide shows, or other sequenced data, media stream 150 is also contemplated to include other forms from streamed data. For example, media stream can also include rendering information for 2-D or 3-D models, simulation information possibly for games, or even sequenced instructions for controlling an application.

Media Stream Access

Figure 2:
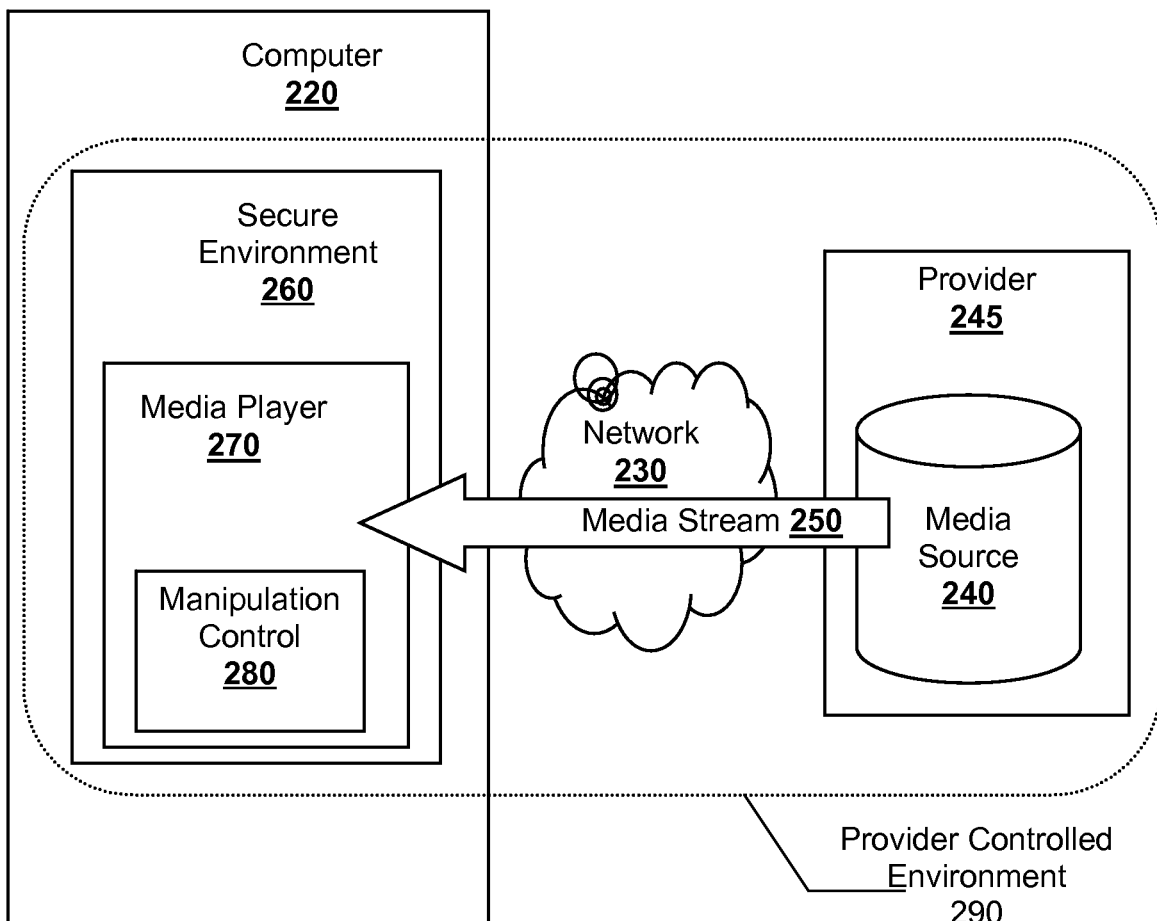
FIG. 2 is a schematic of a system where a media stream can be manipulated in a secure environment.

In FIG. 2, computer 220 represent a platform where media stream 250 can be played when presented to an individual. Provider 245 sends media stream 250 from media source 240 to computer 220 over network 230. In a preferred embodiment, computer 220 comprises secure environment 260 that can remain under control of provider 245. Secure environment 260 ensures media player 270 will only allow an individual to manipulate media stream 250 within the scope of the individual's authorized manipulation rights.

Preferably, computer 220 comprises sufficient processing power, memory, or display for playing media stream 270. Suitable computers include those running a general purpose operating system include variants of Microsoft® Windows®, Linux, Solaris, MacOS®, VxWorks®, BSD, or other operating system. Computer 220 can also comprise a portable device or even a handheld device including a cell phone, PDA, dedicated medical device, or other mobile device.

In a preferred embodiment, computer 220 supports secure environment 260 where media stream 250 can be played. Secure environment 260 has several roles or responsibilities with respect to the media stream 250 and provider 245. Environment 260 enforces manipulation rights granted by provider 245 and ensures computer 220, or an individual operating computer 220, can only manipulate media stream within the scope of the manipulation rights. Example secure environments include Java® execution environments, common language runtimes, VMWare® virtual machines, or other environments. A further example of a secure environment includes those described by U.S. Pat. No. 7,181,617 to Wise et al. A preferred secure environment 260 operates within provider controlled environment 290. For example, when provider 245 authenticates an individual, provider 245 can cause secure environment 260 to be loaded or otherwise activated on computer 220. In a preferred embodiment, secure environment 260 also comprises media play 270 that has been adapted to play media stream 250.

Media player 270 represents one or more software modulus running on computer 220 to play media stream 250. Media player 270 can comprise dedicated software designed to run media stream 270, possibly identified by a mime type associated with media stream 250, or can comprise existing media players including those embedded in web browsers. Example, media players include WinAmp™, gaming software, editing software, Windows Media Center™, Adobe media player, or other existing media players. One should also note that media player 270 can be implemented to take on the roles and responsibilities of secure environment 260. In such an approach, media player 270 is secure environment 260.

One should appreciate that as manipulation rights are recognized as a viable revenue generating resource, the market will seek to adapt media players to offer access to controls operating within the scope of the manipulation rights. Therefore, adapting existing media players or creating media players that respect manipulation rights falls within the scope of the inventive subject matter.

Media Stream Provider

Provider 245 preferably represents an application service provide (ASP) that provides access to one or more of media stream 250. Provider 245 offers access to media stream 250 through one or more interfaces. Example interfaces include database interface, web interfaces through a web server or through a web services API. In a preferred embodiment, once an individual is granted access to media stream 250, media player 270 begins playing media stream 250 by accessing the stream through the interface.

Provider 245 preferably authenticates a remote individual when the individual desires access to media stream 250. An individual can be authenticated using any suitable techniques including using a certificate, OpenID, Kerberos, RADIUS, Diameter, HMAC, PAPI protocol, or other authentication protocols. Provider 245 also authenticates an individual with respect to manipulation rights, possibly using similar authentication techniques.

It should be appreciated that manipulation rights can be differentiated from access rights. Access rights merely grant an individual access to media stream 250. Manipulation rights grant an individual the ability to alter media stream 250. Although manipulation rights are considered distinct from access rights, it is contemplated that manipulation rights can be granted to an individual during initial access authorization. It should also be noted, that each manipulation right or class of manipulation rights could be granted through an additional authorization process after initial access rights have been granted.

Manipulation Rights and Control

Manipulation rights are preferably managed by provider 245. Provider 245 can assign each media stream one or more manipulation rights, possibly binding the rights to media source 240. For example, a patient might decide that medical professionals should have rights to zoom into an X-Ray image. The patient instructs provider to 245 to bind zoom rights to digital files storing the patient's X-Rays. The patient then can authorize various medical professional to use the zoom rights by simply providing the profession with an appropriate password.

Manipulation rights preferably correspond to one or more of manipulation control 280 within provider controlled environment 290 where manipulation control 280 allows an individual to alter media stream 250. In a preferred embodiment, provider 245 unlocks one or more of manipulation control 280 upon proper authorization. In some embodiments manipulation control 280 represents a control within a graphical user interface (GUI), possibly the GUI of media player 270, which becomes accessible when provider 245 grants the manipulation rights or unlocks control 280. In other embodiments, control 280 could include activation of one or more APIs that allow access to software modules or functions offering control over media stream 250.

Manipulation control 280 could also be implemented as one or more software modules provided by provider 245. As manipulation rights are granted, provider 245 sends the modules to computer 220 for use within secure environment 260. When the manipulation rights expire, access to the corresponding control modules can be removed.

Although there could be one-to-one mapping of manipulation control 280 to a manipulation right, other mappings are also contemplated. Manipulation control 280 could map to groups of manipulation rights, possible in a hierarchical fashion. For example, provider 245 could assign a class of "flow control" rights to a media stream file. Once an individual has been authorized with flow control rights, all of controls 280 that fall within the class of flow control become active. Contemplated flow controls rights include a right to stop, play, skip, fast forward, rewind, reverse, seek, record, change source (e.g., change a channel, stations, feed, file, or other source of the stream), or otherwise alter the flow of playing media stream 250.

In addition to allowing alteration of media stream 250 through flow control rights, media stream 250 can also be altered through controlling the display of the media stream, controlling content of the media stream, or other manipulation of media stream 250.

Display controls alter the representation of media stream 250 within media player 270. Contemplated display controls include zoom, enlarge, shrink, rotate, frame grab, print, parental control, picture-in-picture display for displaying multiple streams, or other control that alters the rendering of media stream 250. Display controls can be implemented using suitable graphic display libraries providing scaling, translation, or transformation algorithms. Zoom can be advantageously applied to high definition content where detail is lost when played on low resolution displays. Enlarge and shrink provide for altering the display size. Rotation allows for obtaining different viewing perspectives of rendered models, simulations, or game feeds.

Contemplated content controls allow an individual to alter content associated with media stream 250. Content can include the actual content within media stream 250 or metadata relating to media stream 250. Altering actual content provides for editing content of media stream 250 and can comprise adding content, deleting content, or otherwise changing the content. For example, a doctor viewing a patient's MRI scan session could add an audio track that comprises the doctor's annotations.

Metadata represents data describing media stream 250 as opposed to content carried by the stream. Metadata can be also be added, deleted, or changed without altering how media stream 250 is played. Consider for example, an insurance carrier reviewing a patient's medical records in the form of a media stream. The insurance company could add metadata that indicates that the patient is a client of the company.

One should also note that a manipulated media stream can be advantageously recorded for playback or for long term storage. In some embodiments, provider 245 receives the manipulated stream and records it for future access on media source 240. In other embodiments, the manipulated media stream can be forwarded to other individuals. For example, a consulting doctor could receiving media stream 250 and provide notes in the form a voice track, then forward the stream to a patient's primary healthcare physician.

It should also be appreciated that a manipulation session itself can be recorded without actually altering content of media stream 250. For example, as an individual manipulates media stream 250, computer 220 or provider controlled environment 290 records actions taken by the individual and stores the actions as a macro file that can be played back. The session itself can then be played back by the individual or another individual when accessing media stream 250. Such an approach allows for maintaining integrity of media stream 250 while also providing for alteration of the media stream within secured environment 260. A recorded session can include annotations, display controls, flow control, or other information.

Manipulation rights are also contemplated to comprise a temporal nature where the exercising of the rights is limited with respect to usage or time. In some embodiments, rights are granted for a limited number of usages. For example, a doctor could purchase the ability to record a media stream once so that it is stored locally within secure environment 260. Usage rights can include one-shot rights conferring a single use or can include multiple uses. In other embodiments, rights are granted for an amount of time. Preferred times include at least an hour, or at least a day. However, it is also contemplated that an individual could subscribe to manipulation rights on a monthly, quarterly, or even yearly basis. Once the rights expire, provider 245 can simply deactivate manipulation controls 280.

Access Method of a Media Stream

Figure 3:
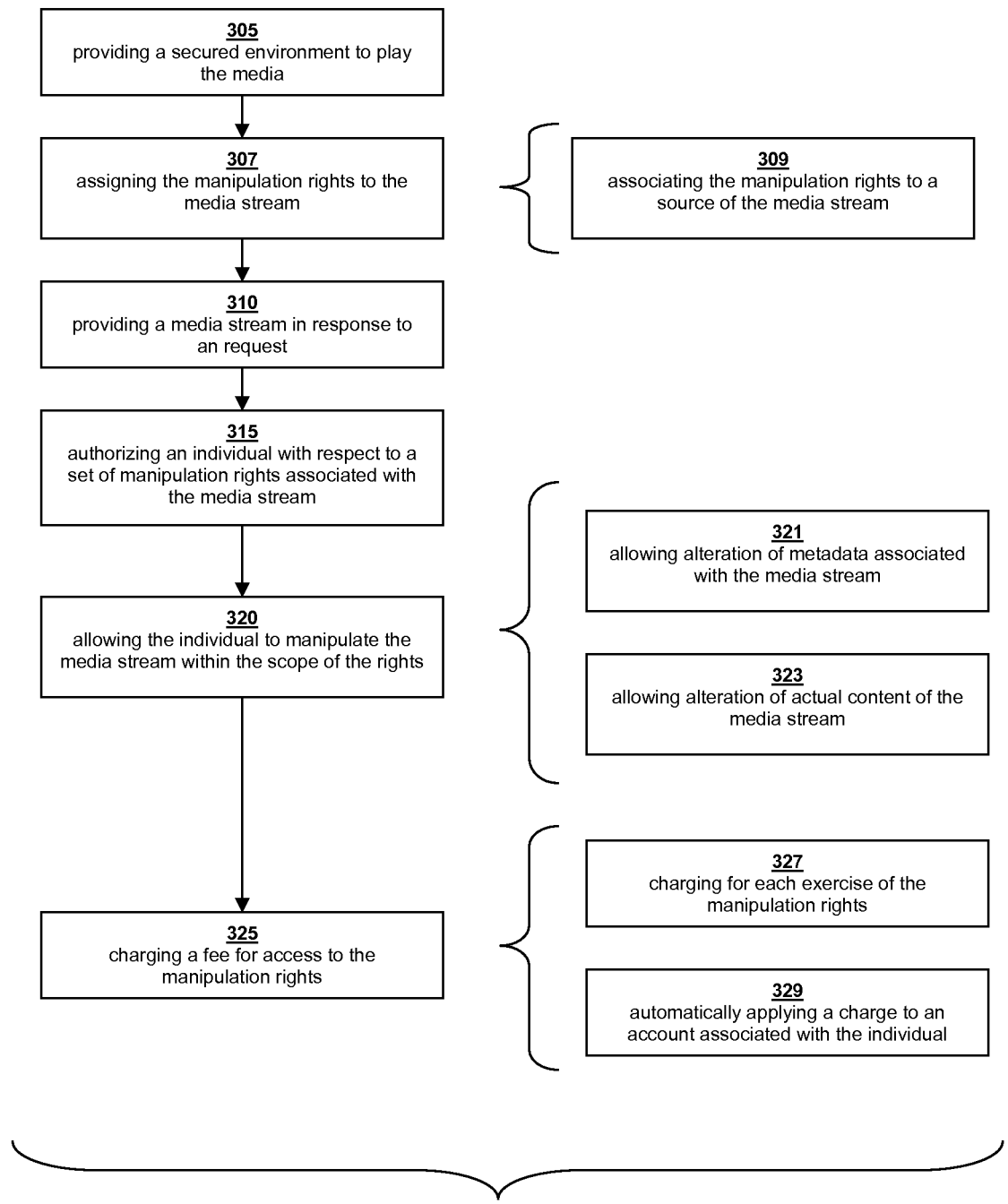
FIG. 3 is a schematic of a method for accessing a media stream.

In FIG. 3, method 300 provides an example set of steps for an individual to access a media stream. Although method 300 is presented as an order set of steps, one should appreciate that that the inventive subject matter is not restricted to the specific order listed. For example, an individual could be charged for access to manipulation rights before they are authorized to use the rights.

At step 305, a secure environment is provided in which a media stream can be played. Although a preferred embodiment employs a secure environment to enforce manipulation rights and to allow a provider to retain control over the media stream, the disclosed techniques can still be applied in systems lacking such an environment. For example, when the contemplated system is deployed within a single company, the need for a secure environment is reduced and might not be necessary.

At step 307 one or more manipulation rights can be assigned to a media stream. The rights can be associated with the stream itself, a media source at step 309, or otherwise coupled to the media stream. Manipulation rights can be coupled to the media stream by including tags that indicate the properties associated with each right. The tags can be stored in an XML file or other structured logically coupled with the media stream. It is also contemplated that the manipulation rights could be assigned through a use of an application specific media play or secure environment. When an individual purchases a desired player, the player itself comprises the desirable manipulation rights in the form of one or more controls.

In response to a request, a provider preferably supplies at least a portion of a media stream as indicated by step 310. Requests can take on nearly form and can include search queries, database queries, or even a purchase request for the media stream. In a preferred embodiment, a medical professional requests a media stream comprising a patient's medical data using a patient ID.

Preferably the provider authorizes the individual at step 315 with respect to a set of one or more manipulation rights associated with the media stream. The provider can authorize the individual using any suitable or well know authentication techniques. It is also contemplated that a third party can also authorize the individual. For example, a centralized authority could provide authentication services between the individual and the provider. In additional, it is contemplated that a patient can authorize a medical profession to access the patient's medical data via a media stream as previously described.

At step 320 the individual is allowed to manipulate the media stream within the scope of the authorized manipulation rights. In a preferred embodiment, manipulation controls are unlocked within a media player to allow the individual access to the controls. In some embodiments, at step 321 the controls allow altering metadata of the media stream. At step 323, altering the actual content of the media stream is allowed as described previously.

In a preferred embodiment, at step 325, a fee is charged for access to the manipulation rights. In a preferred embodiment, the provider charges the fee. However, other third party system could also manage payment transactions.

Fees can be charged based on a number of different methods of accessing the manipulation rights. For example, at step 327 a fee can be charged at each exercise of the manipulation rights. In addition, fees could be charged based on a subscription model where an individual pays for a monthly, quarterly, or yearly access to the manipulation rights. At step 329, fees are preferably automatically charged to an account associated with the individual requesting the media stream. Fees can be tracked and billed automatically by the provider because the provider retains control over the media within the secured environment.

Although a preferred embodiment focuses on delivering medical data streams in a provider controlled manner, it should be appreciated that the disclosed subject matter can be equally and successfully applied to other markets. Alternative embodiments within markets beyond the medical industry include:

(1) Providing first run movies through a media player while restricting recording capabilities.

(2) Providing revenue streams for enhanced control over content including zoom capability, especially for high definition content.

(3) Offering remote audio or video editing systems where many individuals can collaborate with each other without interference by selectively granting manipulation rights to individuals.

(4) Creating a viable peer-to-peer content delivery system (e.g., BitTorrent, LimeWire, etc. . . . ) were media streams can be obtained from multiple sources and where individuals are charged for aggregating pieces of the content within a secure environment.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

I claim:

1. A method of providing dually altered media to a remote computer via a network, the method comprising:
    providing a software modulus to a secure environment of the remote computer within a provider-controlled environment;
    receiving a first request from the remote computer for the media;
    streaming a portion of the media from a data server to the remote computer;
    enabling a first manipulation control of the software modulus within the secure environment under the control of the data server, the first manipulation control configured to manipulate the media within the secure environment;
    enabling a second manipulation control of the software modulus;
    receiving a second request from the second manipulation control to manipulate the media wherein the second request includes an audio track for attachment to the media; and
    streaming altered media to the software modulus in response to the second request from the second manipulation control, wherein the altered media is streamed to the software modulus from outside the secure environment and the altered media includes the audio track and an image file.

2. The method of claim 1, wherein
    the rate of streaming altered media to the software modulus is accelerated relative to the streaming, via the network, the portion of the media to enable fast forward functionality requested by the second manipulation control.

3. The method of claim 2, further comprising the step of zooming, with the first manipulation control, the portion of the media from the data server.

4. The method of claim 3 wherein the zooming the portion of the media step occurs entirely within the secure environment.

5. The method of claim 1, further comprising a provider of the media controlling the secure environment with respect to utilizing at least one of the first and second manipulation controls.

6. The method of claim 1, further comprising the step of decoding, with the software modulus in the secure environment on the computer, the media.

7. The method of claim 1, further comprising the step of rendering, with the software modulus, at least a portion of the media in a picture in picture format with the first manipulation control.

8. The method of claim 1 further comprising the step of disabling one of the first manipulation control and the second manipulation control upon expiration of a first manipulation right, wherein the other of the first manipulation control and the second manipulation control remains enabled following the disabling of one of the first manipulation control and the second manipulation control.

9. The method of claim 1 further comprising the step of forwarding, via the network, the stream of altered media to a second computer that is distinct and separate from the remote computer.

10. The method of claim 1 further comprising the step of enabling, via the network, access rights to the media on the software modulus, wherein the access rights to the media do not enable first manipulation control or the second manipulation control of the software modulus.

11. The method of claim 1 further comprising zooming, with the first manipulation control, the portion of the media; and
zooming, with the second manipulation control, the altered media streamed via the network; and
wherein the step of zooming with the second manipulation control increases the resolution of the media displayed by the software modulus; and step of zooming the first manipulation control increases the size, but not the resolution, of the media displayed by the software modulus.

12. The method of claim 1 further comprising the step of forwarding, via the network, the stream of altered media to a second computer that is distinct and separate from the remote computer.

13. The method of claim 1 further comprising the step of playing the media on the software modulus upon enablement of the access rights, wherein the step of playing the media occurs before the step of enabling the first manipulation control and before the step of enabling the second manipulation control.

14. A method of providing dually altered media to a remote computer via a network, the method comprising:
providing a software modulus to a secure environment of the remote computer within a provider-controlled environment;
receiving a first request from the remote computer for the media;
streaming a portion of the media from a data server to the remote computer;
enabling a first manipulation control of the software modulus within the secure environment under the control of the data server, the first manipulation control configured to manipulate the media within the secure environment;
enabling a second manipulation control of the software modulus;
receiving a second request from the second manipulation control to manipulate the media;
streaming altered media to the software modulus in response to the second request from the second manipulation control, wherein the altered media is streamed to the software modulus from outside the secure environment;
assigning a first manipulation right and a second manipulation right to the media, the first manipulation right associated with the first manipulation control and the second manipulation right associated with the second manipulation control, wherein the step of assigning occurs before the step of receiving, via the network, the first request from the remote computer for the media;
the step of receiving, via the network, the second request from the second manipulation control to manipulate the media includes an audio track for attachment to the media; and
the altered media includes the audio track and an image file.

15. The method of claim 14 wherein the step of assigning the first manipulation right and the second manipulation right to the media includes editing or creating metadata of the media.

16. The method of claim 14 further comprising the step of forwarding, via the network, the stream of altered media to a second computer that is distinct and separate from the remote computer, wherein the second computer lacks an enabled manipulation control associated with the first manipulation right.

17. The method of claim 14 wherein the software modulus is a media player.

18. The method of claim 14 wherein the data server includes a plurality of distributed computers.

* * * * *